United States Patent
Medishetty et al.

(10) Patent No.: US 11,857,556 B2
(45) Date of Patent: Jan. 2, 2024

(54) TOPICAL COMPOSITIONS OF DUTASTERIDE

(71) Applicants: Rajendar Medishetty, Bangalore (IN); Agadihiremath Thippeswamy, Bangalore (IN); Sreenivasa Reddy, Bangalore (IN); Shivakumar Pradeep, Vizianagaram (IN)

(72) Inventors: Rajendar Medishetty, Bangalore (IN); Agadihiremath Thippeswamy, Bangalore (IN); Sreenivasa Reddy, Bangalore (IN); Shivakumar Pradeep, Vizianagaram (IN)

(73) Assignee: SHILPA MEDICARE LIMITED, Karnataka (IN)

( * ) Notice: Subject to any disclaimer, the term of this patent is extended or adjusted under 35 U.S.C. 154(b) by 78 days.

(21) Appl. No.: 17/239,685

(22) Filed: Apr. 26, 2021

(65) Prior Publication Data

US 2022/0347191 A1    Nov. 3, 2022

(51) Int. Cl.
| | |
|---|---|
| *A61K 31/58* | (2006.01) |
| *A61K 9/00* | (2006.01) |
| *A61P 17/14* | (2006.01) |
| *A61K 47/10* | (2017.01) |
| *A61K 47/14* | (2017.01) |
| *A61K 47/44* | (2017.01) |

(52) U.S. Cl.
CPC ............ *A61K 31/58* (2013.01); *A61K 9/0014* (2013.01); *A61K 47/10* (2013.01); *A61K 47/14* (2013.01); *A61K 47/44* (2013.01); *A61P 17/14* (2018.01)

(58) Field of Classification Search
CPC ...... A61K 31/58; A61K 9/0014; A61K 47/10; A61K 47/14; A61K 47/44; A61P 17/14
See application file for complete search history.

(56) References Cited

U.S. PATENT DOCUMENTS

2010/0048598 A1    2/2010   Kandavilli et al.

FOREIGN PATENT DOCUMENTS

WO    2013078259 A2    5/2013

OTHER PUBLICATIONS

Viviscal Hair Expert, Castor Oil for Hair Magic. https://blog.viviscal.com/castor-oil-for-hair-growth/, (Year: 2015).*
Artnaturals, How to use Castor Oil to quickly grow your hair. https://artnaturals.com/blog/how-to-use-castor-oil-to-quickly-grow-your-hair.html (Year: 2017).*
Schneider, Yes, Waterless Shampoo Exists—And It's Revolutionizing Sustainable Hair Care. https://www.mindbodygreen.com/articles/waerless-shampoo-exists-and-its-revolutionizing-sustainable-haircare (Year: 2019).*

* cited by examiner

*Primary Examiner* — Barbara P Badio

(57) ABSTRACT

The present invention relates to a composition for topical application for preventing hair loss, androgenic alopecia (AA) and stimulating hair growth having dutasteride. The composition for topical application for preventing hair loss and stimulating hair growth according to the present invention provides equal or superior hair loss prevention and hair growth stimulating effects while using much smaller dosage than the conventional compositions (oral dosage form) which use finasteride and dutasteride.

1 Claim, No Drawings

TOPICAL COMPOSITIONS OF DUTASTERIDE

FIELD OF THE INVENTION

The present invention relates to compositions for topical application for preventing hair loss, androgenic alopecia and stimulating hair growth comprising 5α-reductase inhibitors, especially dutasteride. The present invention also includes process for preparation of such compositions for topical application and methods of using them.

BACKGROUND OF THE INVENTION

According to the studies conducted so far, it has been found that the causes of hair loss include endocrine system disorders such as hormonal imbalance; excessive sebum formation caused by circulatory system disorders such as autoimmune nervous system disorders, blood circulation disorders; nutritional deficiency of hair roots, allergies, bacterial infections, genetic factors psychological stress, environmental factors such as atmospheric pollution or foods, and aging etc.

The products which are sold as hair growth stimulating agents or hair loss preventing agents on hair include growth period inducing effects, hair growth period extending effects, 5α-reductase inhibitory effects, blood circulation promoting effects, antiseptic effects, anti-dandruff effects, moisturizing effects, antioxidant effects etc., but the effects of preventing hair loss and stimulating hair growth of conventional agents are not sufficient.

Male pattern alopecia is dependent on male hormones and is thus directly related to the amount of male hormones. 5α-reductase is an enzyme that is responsible for conversion of testosterone, a male sex hormone, to dihydrotestosterone (DHT). DHT is an androgenic compound that causes hyperandrogenic conditions like enlargement of the prostate in men with progressing age, termed "benign prostatic hyperplasia". Another consequence of increased DHT levels includes androgenic alopecia (AA), which is commonly termed "male pattern baldness." The cause of male pattern alopecia is synthesis of excessive DHT by action of 5α-reductase, and thus it is possible to fundamentally and effectively prevent and treat male pattern alopecia by inhibiting the activity of 5α-reductase.

Currently, two treatments are approved by U.S. Food and Drug Administration for the treatment of androgenic alopecia (AA) in males: topical minoxidil and oral finasteride. While minoxidil (having a chemical name 6-piperidin-1-ylpyrimidine-2,4-diamine 3-oxide) is an arterial vasodilator, finasteride is a type II 5α-reductase inhibitor.

The minoxidil was developed for the purpose of lowering blood pressure of hypertensive patients, but it is most widely used as hair growth drug since its use changed due to hair growth side-effects that occurred during the use. The mechanism of action of minoxidil has not been clearly elucidated. However, the mechanism of action of minoxidil has been explained by a hypothesis that the minoxidil increases blood flow to the follicles to cause an increase in blood flow, thus stimulating the growth of hair, and a hypothesis that the minoxidil acts directly on the follicular epithelium to induce the growth of hair. However, hair restorers comprising minoxidil should be applied several times daily to maintain the hair growth effect, which is very cumbersome and easy to forget. Therefore, in many cases, the hair growth effect is not sufficiently obtained due to irregular application and arbitrary discontinuation of treatment.

Finasteride is a drug that inhibits 5α-reductase type II which converts testosterone, one of the male hormones, into DHT that causes hair loss. Oral finasteride 1 mg causes the possible sexual side effects, which is used for the male pattern alopecia, even after discontinuation of use. Therefore, USFDA recommended the attention of medical professionals and patients. As a result of reviewing the post-marketing cases reported on the FDA's Adverse Event Reporting System (AERS) and safety databases of marketed products, it was found that some sexual function-related adverse reactions (such as hyposexuality, ejaculation disorders, orgasmic disorders etc.) continued even after discontinuation of use.

One more compound in the 5α-reductase inhibitor class is dutasteride. Dutasteride has a chemical name (5α,17β)-N-{2,5-bis(trifluoromethyl)phenyl}-3-oxo-4-azaandrost-1-ene-17-carboxamide. The structural formula is represented as below.

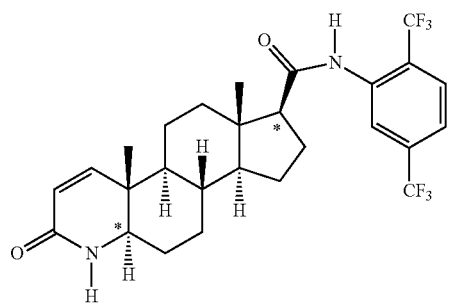

Dutasteride is a synthetic 4-azasteroid compound that is a selective inhibitor of both type I and type II isoforms of steroid 5α-reductase (5AR), an intracellular enzyme that converts testosterone to 5α-dihydrotestosterone (DHT), and is indicated for the treatment of symptomatic benign prostatic hyperplasia (BPH) in men. A pharmaceutical product containing dutasteride as the active ingredient is commercially available as AVODART®, which is approved by USFDA from GlaxoSmithKline, in the form of soft gelatin capsules for oral administration and containing 0.5 mg of the active ingredient. Oral Dutasteride has been approved by Ministry of Food and Drug Safety; South Korea for the treatment of male pattern baldness (androgenic alopecia) at dosage of 0.5 mg once daily.

Dutasteride is a highly lipophilic molecule (Log P=6.8). It is insoluble in water, soluble in ethanol, methanol and polyethylene glycol 400. Absolute bioavailability of orally administered dutasteride is only about 60% (40%-94%). Some of the known approaches to improve solubility characteristics and bioavailability of drug compounds include salt formation, particle size reduction, pH adjustment, use of surfactants, inclusion complexes with cyclodextrins, use of oily formulations, use of self-emulsifying drug delivery systems, formation of co-precipitates with hydrophilic polymers, and co-milling with hydrophilic excipients, to name a few.

5α-reductase inhibitors block conversion of testosterone to dihydrotestosterone (DHT), a potent androgen. Systemic administration 5α-reductase inhibitors suppress level of DHT in blood, thereby there are chances of sexual side effects. Oral Finasteride and dutasteride currently approved for androgenic alopecia causes sexual side effects on long term use.

US Patent Publication No. 20100048598 discloses the pharmaceutical composition for topical application comprising dutasteride or pharmaceutically acceptable salt, ester, derivative thereof, and a pharmaceutically acceptable carrier, and optionally one or more other pharmaceutically acceptable excipients. Further US '598 Publication discloses the pharmaceutical compositions for topical application comprising 0.5 wt % of dutasteride.

The present invention has been made to solve the above problems of the prior art, and an object of the present invention is to provide a composition of dutasteride for topical application for preventing hair loss and stimulating hair growth, which has the following advantages
1. It provides the effects of preventing hair loss and stimulating hair growth that are equal to or higher than that of conventional treatment agents (oral dutasteride & finasteride) even though the amount of dutasteride used is less than one half, more preferably less than two fifth that of the conventional treatment agents (oral dutasteride and finasteride).
2. There are almost no systemic side effects of the conventional treatment agents (oral dutasteride and finasteride).
3. It is possible to effectively prevent hair loss from the beginning of the treatment due to a rapid onset of the effect; and
4. It provides almost 100% effect to patients with hair loss, unlike the conventional prescription (oral dutasteride and finasteride) that provides about 70% effect.

OBJECTS OF THE INVENTION

The object of the present invention is to provide a composition for topical application for preventing hair loss and stimulating hair growth, containing dutasteride or a pharmaceutically acceptable salt thereof.

Another object of the present invention is to provide a composition for topical application for preventing hair loss and stimulating hair growth, comprising dutasteride, wherein the effects of preventing hair loss and stimulating hair growth that are equal to or higher than that of conventional oral treatment agents (oral finasteride and oral dutasteride) even though the amount of dutasteride is much less (less than one half, more preferably less than two fifth) that of conventional oral treatment agents (oral finasteride and oral dutasteride).

A further object of the present invention is to provide a composition for topical application for preventing hair loss and stimulating hair growth, comprising dutasteride, wherein the topical compositions uses small amount of dutasteride and thus has little side-effects such has hyposexuality, impotence, ejaculation disorder etc. Further, it can effectively prevent hair loss from the beginning of treatment due to a fast onset of the effect than the use of a conventional oral 5α-reductase inhibitor (oral finasteride and dutasteride) and can provide the effect of improving treatment compliance of patients. Furthermore, it provides almost 100% effect to hair loss patients, unlike the conventional prescription that is effective only for about 70% of hair loss patients.

SUMMARY OF THE INVENTION

The present invention relates to a composition for topical application for preventing hair loss and stimulating hair growth, comprising 5α-reductase inhibitors, especially dutasteride or pharmaceutically acceptable salts thereof.

In embodiments of the invention the present invention provides pharmaceutical compositions for improved topical delivery of dutasteride, including salts, esters, isomers, solvates, hydrates, and polymorphs thereof.

The daily dose of the dutasteride contained in the topical application for preventing hair loss and stimulating hair growth, administered is about 0.1 mg to about 0.5 mg, preferably of about 0.25 mg, most preferably of about 0.2 mg; which preferably less than about one half and most preferably less than two fifth that of oral dutasteride (0.5 mg), a currently commercially available 5α-reductase inhibitor (the daily dose of commercially available oral dutasteride is 0.5 mg and oral finasteride is 1 mg).

The present invention provides a composition for topical application for preventing hair loss and stimulating hair growth, the composition comprising dutasteride or pharmaceutically acceptable salt thereof, medium chain triglycerides, castor oil and ethanol, wherein dutasteride contained in the topical application is administered at a daily dose of about 0.1 to about 0.5 mg.

In another embodiment the present invention further provides a composition for topical application for preventing hair loss and stimulating hair growth, the composition comprising of about 0.01 wt % to about 0.06 wt % of dutasteride, about 25 wt % to about 35 wt % of medium chain triglycerides, about 25 wt % to about 35 wt % of ethanol and about 35 wt % to about 45 wt % of castor oil based on total weight of the composition, wherein dutasteride contained in the composition is in an amount to provide a daily dose of about 0.1 to about 0.5 mg.

In a further embodiment the present invention further provides a composition for topical application for preventing hair loss and stimulating hair growth, the composition comprising of about 0.022 wt % (equivalent to 0.02% w/v) of dutasteride, about 30 wt % of medium chain triglycerides, about 30 wt % of ethanol and about 40 wt % of castor oil based on total weight of the composition.

In another embodiment the present invention further provides a composition for topical application for preventing hair loss and stimulating hair growth, the composition consisting of about 0.022 wt % (equivalent to 0.02% w/v) of dutasteride, about 30 wt % of medium chain triglycerides, about 30 wt % of ethanol and about 40 wt % of castor oil based on total weight of the composition.

In one embodiment of the invention, pharmaceutical compositions of the present invention are in the form of solutions, ointments, creams, gels, lotions, suspensions, mousses, aerosols, sprays, foams, microspheres, microemulsions, nanoemulsions, nanoparticles, nanosuspensions, dermal sticks, roll-ons, pumps, patches, tapes, or the like.

In an embodiment, pharmaceutical compositions of the present invention exhibit excellent physicochemical stability during storage at conditions of 40° C. and 75% relative humidity (RH) over a period of at least 6 months.

In another embodiment the present invention provides methods of using pharmaceutical compositions described herein, for the prophylaxis, amelioration, and/or treatment of androgenic alopecia.

In another embodiment, pharmaceutical compositions of the present invention comprise dutasteride as an active agent, which is useful in the prophylaxis, amelioration or treatment of androgenic alopecia, and additionally comprise at least one another active agent.

DETAILED DESCRIPTION OF THE INVENTION

The present invention relates to a composition for topical application for preventing hair loss and stimulating hair growth, comprising a 5α-reductase inhibitor especially dutasteride or a pharmaceutically acceptable salt thereof. In embodiments, the present invention provides pharmaceutical compositions for improved topical delivery of dutasteride, including salts, esters, isomers, solvates, hydrates and polymorphs thereof.

The daily dose of the dutasteride contained in the topical application for preventing hair loss and stimulating hair growth, administered is about 0.1 mg to about 0.5 mg, preferably of about 0.25 mg, most preferably of about 0.2 mg; which is preferably less than about one half and most preferably less than two fifth that of oral dutasteride (0.5 mg), a currently commercially available 5α-reductase inhibitor (the daily dose of commercially available oral dutasteride is 0.5 mg and oral finasteride is 1 mg).

If the daily dose of dutasteride is less than 0.1 mg, the onset of the effect is insignificant, whereas, if it exceeds 0.5 mg, side effects such as hyposexuality, ejaculation decrease etc., may occur. The daily dose of dutasteride for topical administration is preferably 0.4 mg, more preferably 0.25 mg and most preferably 0.2 mg. If the dose of dutasteride is out of the range, the effect is insufficient or side effects may occur.

In embodiments of the invention, the present invention relates to a composition for topical administration comprising dutasteride, or pharmaceutically acceptable salts or solvates thereof and pharmaceutically acceptable excipients. Pharmaceutically acceptable excipients of the present invention are hydrophilic, hydrophobic, lipophilic, or amphiphilic.

In embodiments of the invention pharmaceutically acceptable excipients include, but are not limited to, penetration enhancers, oily vehicles, antioxidants, buffering agents, preservatives, viscosity modifying agents, chelating/complexing agents, colouring agents, perfumes, polymers, gelling agents, surfactants, co-surfactants, alcohols, liquid or semi-solid oily components, and any mixtures thereof.

Dutasteride has side effects such as hyposexuality, impotence, ejaculation disorder etc. Therefore, it is required to reduce these side effects. In embodiments of the invention, the present invention relates to a composition for topical administration comprising dutasteride, at least one penetration enhancer, and an oily vehicle. The topical composition comprising dutasteride, at least one penetration enhancer and an oily vehicle is topically applied at the target, and the inventors of the present invention have surprisingly found that dutasteride is effectively delivered to the target that provides almost 100% effect to hair loss patients, and provide very rapid and excellent effects even though the amount of dutasteride is less than two fifth of the conventional oral dutasteride (0.5 mg once daily).

The composition for topical application for preventing hair loss and stimulating hair growth may be prepared, comprising dutasteride or pharmaceutically acceptable salt thereof in an amount of about 0.1 mg to about 0.5 mg, more preferably 0.15 mg to 0.4 mg, and most preferably 0.2 mg with respect to 1 ml of the composition for topical application. It is preferable that the composition for topical application prepared in the above manner is applied in an amount of 1 ml once or twice a day, most preferably 1 ml once daily containing 0.2 mg of dutasteride.

The present invention relates to the compositions for topical application for preventing hair loss and stimulating hair growth, comprising dutasteride, at least one penetration enhancer and an oily vehicle.

In embodiments of the invention dutasteride is present in the range from about of 0.001 wt % to about 0.5 wt %, preferably in the range of about 0.01 wt % to about 0.1 wt %, more preferably from about 0.01 wt % to about 0.06 wt % and most preferably 0.022 wt % (equivalent to 0.02% w/v) based on the total weight of the composition.

Suitable penetration enhancers that can be used in the present invention include, but are not limited to: medium chain triglycerides of caprylic ($C_8$) and capric ($C_{10}$) acids (available commercially as LABRAFAC™) sulfoxides such as dimethylsulfoxide (DMSO) and decylmethylsulfoxide (C10 MSO); ethers such as diethylene glycol monoethyl ether (available commercially as TRANSCUTOL') and diethylene glycol monomethyl ether; 1-substituted azacycloheptan-2-ones, such as 1-n-dodecyl-cyclazacycloheptan-2-one; alcohols such as ethanol, propanol, octanol, benzyl alcohol, and the like; fatty acids such as lauric acid, oleic acid, and valeric acid; fatty acid esters such as isopropyl myristate, isopropyl palmitate, methylpropionate, and ethyl oleate; polyol esters such as butanediol and polyethylene glycol monolaurate, amides and other nitrogenous compounds such as urea, N,N-dimethylacetamide (DMA), N,N-dimethylformamide (DMF), 2-pyrrolidone, 1-methyl-2-pyrrolidone, ethanolamine, diethanolamine, and triethanolamine; terpenes and terpinoids; alkanones; organic acids, such as salicylic acid and salicylates, citric acid and succinic-acid and the like; and any mixtures thereof. The most preferably used penetration enhancer is mixture of medium chain triglycerides and ethanol. The penetration enhancers are preferably used in the range of about 20 wt % to about 80 wt % to the total weight of the composition. Preferably medium chain triglycerides are used in the range of about 25 wt % to about 35 wt %, most preferably about 30 wt % based on the total weight of the composition. Preferably ethanol is used in the range of about 25 wt % to about 35 wt %, most preferably about 30 wt % based on the total weight of the composition.

Examples of the oily vehicle include glycerin esters of fatty acids such as mono- or tri-glycerides of fatty acids, including their polyethylene glycol complex, polyethylene glycol or propylene glycol esters of fatty acids or vegetable oils; vegetable oils, including their hydrogenated form, such as sesame oil, soybean oil, castor oil, corn oil, palm oil, peanut oil, cacao oil, cotton seed oil, sunflower seed oil, safflower oil, almond oil or olive oil; fatty acids and fatty alcohols, and their esters, such as oleic acid, linolenic acid, linoleic acid, palmitic acid, palmitoleic acid, arachidonic acid, myristic acid, capric acid, caprylic acid, lauric acid, stearic acid, lauryl alcohol, oleyl alcohol, cetyl alcohol, stearyl alcohol, ethyl oleate, oleyl laurate, isopropyl myristate, isopropyl palmitate, 2-octyldodecyl myristate or cetyl palmitate; and a mixture thereof. The most preferred oily vehicle used in the present composition is castor oil. Preferably castor oil is used in the range of about 35 wt % to about 45 wt %, most preferably about 40 wt % based on the total weight of the composition.

The present invention relates to a composition for topical application for preventing hair loss and stimulating hair growth, the composition comprising of about 0.01 wt % to about 0.06 wt % of dutasteride, about 25 wt % to about 35 wt % of medium chain triglycerides, about 25 wt % to about 35 wt % of ethanol and about 35 wt % to about 45 wt % of castor oil based on total weight of the composition, wherein dutasteride contained in the composition is in an amount to provide a daily dose of about 0.1 to about 0.5 mg.

The present invention relates to a composition for topical application for preventing hair loss and stimulating hair growth, the composition comprising of about 0.022 wt % (equivalent to 0.02% w/v) of dutasteride, about 30 wt % of medium chain triglycerides, about 30 wt % of ethanol and about 40 wt % of castor oil based on total weight of the composition.

The present invention further relates to a composition for topical application for preventing hair loss and stimulating hair growth, the composition consisting of about 0.022 wt % (equivalent to 0.02% w/v) of dutasteride, about 30 wt % of medium chain triglycerides, about 30 wt % of ethanol and about 40 wt % of castor oil based on total weight of the composition.

Antioxidants that are useful in the present invention include, but are not limited to, tocopherol succinate, ascorbic acid, propyl gallate, vitamin E, butylated hydroxytoluene, butylated hydroxyanisole, including any mixtures thereof.

Buffering agents that are useful in the present invention include, but are not limited to: alkali metal salts such as potassium and sodium carbonates, acetates, borates, phosphates, citrates and hydroxides; weak acids such as acetic, boric and phosphoric acids, and the like; and mixtures thereof.

Preservatives that are useful in the present invention include, but are not limited to, methyl, ethyl, propyl and butyl esters of p-hydroxybenzoic acid (parabens), and the like, including any mixtures thereof.

Viscosity modifying agents that are useful in the present invention include, but are not limited to, cetyl alcohol, glycerol, polyethylene glycol (PEG), PEG-stearate, xanthan gums and the like, including any mixtures thereof.

Chelating or complexing agents that are useful in the present invention include but are not limited to ethylenediaminetetraacetic acid (EDTA) and its derivatives, including mixtures thereof.

In one embodiment of the invention, pharmaceutical compositions of the present invention are in the form of solutions, ointments, creams, gels, lotions, suspensions, mousses, aerosols, sprays, foams, microspheres, microemulsions, nanoemulsions, nanoparticles, nanosuspensions, dermal sticks, roll-ons, pumps, patches, tapes, or the like.

In an embodiment, pharmaceutical compositions of the present invention exhibit excellent physicochemical stability during storage at conditions of 40° C. and 75% relative humidity (RH) over a period of at least 6 months.

In embodiments of the present invention provides methods of using pharmaceutical compositions described herein, for the prophylaxis, amelioration, and/or treatment of androgenic alopecia.

In embodiments of the present invention, pharmaceutical compositions provide topical delivery of dutasteride to enhance the availability of the active agent to the hair follicles in the scalp, particularly when applied onto the scalp.

In embodiments, pharmaceutical compositions of the present invention, upon administration, permit the drug to penetrate through the skin or the scalp, and it blocks 5α-reductase locally in scalp and no significant systemic DHT levels.

Pharmaceutical compositions of the present invention comprising at least one 5α-reductase inhibitor as an active agent, can additionally comprise at least one another active agent. Such other active agents can either enhance or potentiate the activity of a 5α-reductase inhibitor or are useful for management (prophylaxis, amelioration or treatment) of any associated diseases/disorders, for which said 5α-reductase inhibitors are indicated. In certain embodiments, such additional active agents may be chemical compounds or extracts of one or more active components obtained from a natural source, such as plant extracts.

The additional active agents include but are not limited to: hair loss preventing agents; hair growth promoting agents; anti-alopecia agents such as finasteride, FCE 28260, and minoxidil; anti-infectives; antibacterials; antifungals; antihistaminics; immunomodulatory agents; anti-dandruff agents; antivirals; antiandrogenic agents such as fluconazole, ketoconazole and spironolactone; hormones; steroids; and the like.

In embodiments of the invention present invention provide methods for preparing pharmaceutical compositions of the present invention. In an embodiment, a process for preparation of a composition of the present invention comprises combining the dutasteride with at least one pharmaceutically acceptable excipients, and formulating into a suitable topical dosage form.

In an embodiment, a method of preparing a pharmaceutical composition of the present invention comprises
 (a) dissolving dutasteride in ethanol
 (b) adding the medium chain triglycerides and castor oil to contents of step a
 (c) forming the mixture into a solution.

The methods of manufacturing of the present invention may include filling compositions of the present invention into appropriate containers. The compositions of the present invention may be packaged, for example, into unit dose or multi-dose containers.

The following examples further describe certain specific aspects and embodiments, are provided solely for purposes of illustration, and should not be construed as limiting the scope of the invention in any manner.

EXAMPLE 1: Solution Composition Containing Dutasteride for Topical Application for Preventing Hair Loss and Stimulating Hair Growth

TABLE 1

| Ingredient | Percent (w/w) |
| --- | --- |
| Dutasteride | 0.005-1% |
| Castor Oil | 30-50% |
| Medium Chain Triglycerides | 25-35% |
| Ethanol | 25-35% |

Process for Preparation
1. Dutasteride was dissolved in ethanol
2. Medium chain triglycerides and castor oil was added to contents of step 1 to form the solution.
3. The above solution was filled into suitable containers.

EXAMPLES 2 to 4: Composition of Topical Application of Dutasteride

TABLE 2

| Ingredient | Ex.2 Wt % | Ex.3 Wt % | Ex.4 Wt % |
| --- | --- | --- | --- |
| Dutasteride* | 0.011 | 0.022 | 0.056 |
| Castor Oil | 40 | 40 | 40 |
| Medium Chain Triglycerides | 30 | 30 | 30 |
| Ethanol | q.s to 100 | q.s to 100 | q.s to 100 |

*equivalent to 0.01% w/v, 0.02% w/v & 0.05% w/v for Ex.2, Ex.3 & Ex.4 respectively.

Process for Preparation
1. Dutasteride was dissolved in ethanol
2. Medium chain triglycerides and castor oil was added to contents of step 1 to form the solution.
3. The above solution was filled into suitable containers.

EXAMPLES 5 to 7: Composition of Topical Application of Dutasteride

TABLE 3

| Ingredient | Ex.5 Wt % | Ex.6 Wt % | Ex.7 Wt % |
|---|---|---|---|
| Dutasteride* | 0.012 | 0.024 | 0.061 |
| Castor Oil | 12.5 | 12.5 | 12.5 |
| Medium Chain Triglycerides | 12.5 | 12.5 | 12.5 |
| Ethanol | q.s to 100 | q.s to 100 | q.s to 100 |

*equivalent to 0.01% w/v, 0.02% w/v & 0.05% w/v for Ex.5, Ex.6 & Ex.7 respectively.

Process for Preparation
1. Dutasteride was dissolved in ethanol
2. Medium chain triglycerides and castor oil was added to contents of step 1 to form the solution.
3. The above solution was filled into suitable containers.

EXAMPLES 8 to 10: Composition of Topical Application of Dutasteride

TABLE 4

| Ingredient | Ex.8 Wt % | Ex.9 Wt % | Ex.10 Wt % |
|---|---|---|---|
| Dutasteride* | 0.011 | 0.021 | 0.054 |
| Castor Oil | 75 | 75 | 75 |
| Medium Chain Triglycerides | 12.5 | 12.5 | 12.5 |
| Ethanol | q.s to 100 | q.s to 100 | q.s to 100 |

*equivalent to 0.01% w/v, 0.02% w/v & 0.05% w/v for Ex.8, Ex.9 & Ex.10 respectively.

Process for Preparation
1. Dutasteride was dissolved in ethanol
2. Medium chain triglycerides and castor oil was added to contents of step 1 to form the solution.
3. The above solution was filled into suitable containers.

EXAMPLES 11 to 13: Composition of Topical Application of Dutasteride

TABLE 5

| Ingredient | Ex.11 Wt % | Ex.12 Wt % | Ex.13 Wt % |
|---|---|---|---|
| Dutasteride* | 0.011 | 0.022 | 0.054 |
| Castor Oil | 12.5 | 12.5 | 12.5 |
| Medium Chain Triglycerides | 75 | 75 | 75 |
| Ethanol | q.s to 100 | q.s to 100 | q.s to 100 |

*equivalent to 0.01% w/v, 0.02% w/v & 0.05% w/v for Ex.11, Ex.12 & Ex.13 respectively.

Process for Preparation
1. Dutasteride was dissolved in ethanol
2. Medium chain triglycerides and castor oil was added to contents of step 1 to form the solution.
3. The above solution was filled into suitable containers.

Comparative Example 1

In comparative example 1, Finasteride active ingredient was dissolved to prepare compositions comprising the oral medication using the following ingredients as shown in Table 6.

TABLE 6

| Ingredient | Comparative Example 1 |
|---|---|
| Finasteride | 0.1 mg |
| Polyethylene Glycol 400 | 0.060 ml |
| Purified water | Qs to 1 ml |

Oral Finasteride medication administered in rats at 0.1 mg/kg corresponds to 1 mg human dose.

TEST EXAMPLE 1: Pre-Clinical Trials of Preventing Hair Loss and Stimulating Hair Growth (Evaluation of Changes in Hair Growth and Thickness)

The hair growth and hair thickness measurement of was conducted in Wistar rats. Wistar rats was divided into groups, each group having 13 animals. The study on the Wistar rats was conducted for 21 days. On day "0" of the study, fur over and around the flank organs of Wistar rats was shaved with electric clippers and the area of 2×2 cm was used for topical application of dutasteride compositions of examples 2 to 13 at a dose of 100 μl/kg of example 2 to Example 13 along with the compositions of reference example 1 (Finasteride oral at a dose of 0.1 mg/kg) for a period of 21 days once daily (every day between 10 and 11 pm). 100 μl of 1% testosterone was injected subcutaneously daily for 21 days (at 9 am every day) and effect (hair growth and thickness) was evaluated on $22^{nd}$ day after sacrificing the animals. The normal control of shaved rats (without the administration of testosterone) was placed with a group consisting of 13 animals.

The change in hair growth was measured by visual scoring (hair growth score) on the 13 animals of each group and the mean was calculated. The visual scoring was calculated based on following parameters Score 0: no hair growth observed Score 1: less than 20% growth observed Score 2: 20% to less than 40% growth observed Score 3: 40% to less than 60% growth observed Score 4: 60% to less than 80% growth observed Score 5: 80% to 100% growth The visual scoring of mean of 13 animals in each group treated with compositions of example 2 to 13 along with reference oral finasteride and normal control was depicted in Table 7.

The hair thickness was measured by Caslite hair analysing instrument attached to microscope at 200× magnification and results of hair thickness (μm) in each group treated with compositions of example 2 to 13 along with reference oral finasteride and normal control was depicted in Table 7.

TABLE 7

| Example No | Composition | Hair growth score | Hair thickness (μm) |
|---|---|---|---|
| 2 | Dutasteride 0.011 wt % (0.01% w/v) Castor Oil 40 wt % Medium chain triglycerides 30 wt % Ethanol-qs to 100 wt % | 4.15 | 62.08 |
| 3 | Dutasteride 0.022 wt % (0.02% w/v) Castor Oil 40 wt % Medium chain triglycerides 30 wt % Ethanol-qs to 100 wt % | 4.85 | 67.92 |
| 4 | Dutasteride 0.056 wt % (0.05% w/v) Castor Oil 40 wt % Medium chain triglycerides 30 wt % Ethanol-qs to 100 wt % | 4.69 | 58 |
| 5 | Dutasteride 0.012 wt % (0.01% w/v) Castor Oil 12.5 wt % Medium chain triglycerides 12.5 wt % Ethanol-qs to 100 wt % | 4.08 | 56.92 |
| 6 | Dutasteride 0.024 wt % (0.02% w/v) Castor Oil 12.5 wt % Medium chain triglycerides 12.5 wt % Ethanol-qs to 100 wt % | 3.69 | 60.08 |
| 7 | Dutasteride 0.061 wt % (0.05% w/v) Castor Oil 12.5 wt % Medium chain triglycerides 12.5 wt % Ethanol-qs to 100 wt % | 4.15 | 61.54 |
| 8 | Dutasteride 0.011 wt % (0.01% w/v) Castor Oil 75 wt % Medium chain triglycerides 12.5 wt % Ethanol-qs to 100 wt % | 3.38 | 43.15 |
| 9 | Dutasteride 0.021 wt % (0.02% w/v) Castor Oil 75 wt % Medium chain triglycerides 12.5 wt % Ethanol-qs to 100 wt % | 3.85 | 59 |
| 10 | Dutasteride 0.054 wt % (0.05% w/v) Castor Oil 75 wt % Medium chain triglycerides 12.5 wt % Ethanol-qs to 100 wt % | 3.54 | 50.85 |
| 11 | Dutasteride 0.011 wt % (0.01% w/v) Castor Oil 12.5 wt % Medium chain triglycerides 75 wt % Ethanol-qs to 100 wt % | 3.31 | 49.23 |
| 12 | Dutasteride 0.022 wt % (0.02% w/v) Castor Oil 12.5 wt % Medium chain triglycerides 75 wt % Ethanol-qs to 100 wt % | 4.08 | 55.23 |
| 13 | Dutasteride 0.054 wt % (0.05% w/v) Castor Oil 12.5 wt % Medium chain triglycerides 75 wt % Ethanol-qs to 100 wt % | 3.69 | 45.69 |
| Reference Example 1 | Finasteride oral | 4.85 | 64.75 |
| Normal Control | Normal Control | 4.46 | 66 |

The data in the Table 7 shows the hair growth score and hair thickness increased significantly in the Wistar rats of example 2 to 4, most preferably the composition of example 3 consisting of Dutasteride 0.022 wt % (equivalent to 0.02% w/v), Castor Oil 40 wt %, Medium chain triglycerides 30 wt % and Ethanol: qs to 100 wt % (about 30 wt %) has highest hair growth score and hair thickness when compared to the other formulations. The rapid onset of the effects of the above described composition for topical application of the present invention can significantly improve the treatment compliance. That is, in case of the conventional preparations (finasteride oral) the onset of effects is similar to that of the formulation as disclosed in example 3 at the reduced dosage with topical administration and has little side-effects, when compared to the oral finasteride.

The invention claimed is:

1. A topical composition for stimulating hair growth, the composition consisting of
   (a) about 0.056 wt % (equivalent to 0.05% w/v) dutasteride,
   (b) about 30 wt % of medium chain triglycerides,
   (c) about 30 wt % of ethanol and
   (d) about 40 wt % of castor oil based on the total weight of the composition, wherein dutasteride contained in the composition is in an amount to provide a daily dose of about 0.1 to about 0.5 mg.

* * * * *